United States Patent
Morin et al.

(10) Patent No.: US 10,060,848 B2
(45) Date of Patent: Aug. 28, 2018

(54) OPTICAL FILTERING DEVICE FOR DETECTING GAS

(71) Applicant: BERTIN TECHNOLOGIES, Montigny le Bretonneux (FR)

(72) Inventors: Nathalie Morin, Trets (FR); Philippe Bernascolle, Tourves (FR); Franck Fervel, Peynier (FR); Guillaume Druart, Palaiseau (FR)

(73) Assignee: BERTIN TECHNOLOGIES, Montigny le (FR)

( * ) Notice: Subject to any disclaimer, the term of this patent is extended or adjusted under 35 U.S.C. 154(b) by 0 days.

(21) Appl. No.: 15/534,571

(22) PCT Filed: Dec. 11, 2015

(86) PCT No.: PCT/FR2015/053456
§ 371 (c)(1),
(2) Date: Jun. 9, 2017

(87) PCT Pub. No.: WO2016/092236
PCT Pub. Date: Jun. 16, 2016

(65) Prior Publication Data
US 2017/0336322 A1    Nov. 23, 2017

(30) Foreign Application Priority Data
Dec. 12, 2014    (FR) ...................... 14 62391

(51) Int. Cl.
*G01N 21/35*    (2014.01)
*G01N 21/3518*    (2014.01)

(52) U.S. Cl.
CPC ................. *G01N 21/3518* (2013.01)

(58) Field of Classification Search
CPC .................................................. G01N 21/3518
See application file for complete search history.

(56) References Cited

U.S. PATENT DOCUMENTS

| | | | |
|---|---|---|---|
| 4,498,012 A | 2/1985 | Duda | 250/578 |
| 5,163,332 A | 11/1992 | Wong | |
| 5,306,913 A | 4/1994 | Noack et al. | 250/338.5 |
| 5,340,986 A | 8/1994 | Wong | |
| 2009/0104406 A1 | 4/2009 | Rivero | 428/138 |
| 2013/0135470 A1 | 5/2013 | Prata et al. | |

FOREIGN PATENT DOCUMENTS

| | | | |
|---|---|---|---|
| CN | 1075549 A | 8/1993 | |
| CN | 101153832 A | 4/2008 | |
| CN | 102981199 A | 3/2013 | |
| CN | 103038646 A | 4/2013 | |
| CN | 203385658 U | 1/2014 | |
| CN | 104007081 A | 8/2014 | |
| EP | 0544962 | 12/1991 | ............. G01N 21/35 |
| WO | WO 03/044499 | 5/2003 | ............. G01N 21/35 |

OTHER PUBLICATIONS

International Search Report from corresponding International Patent Application No. PCT/FR15/53456, dated Mar. 8, 2016.

*Primary Examiner* — Mark R Gaworecki
(74) *Attorney, Agent, or Firm* — Kusner & Jaffe

(57) ABSTRACT

An optical filtering device, in particular for remote gas detection, including a member comprising a tubular passage accommodating a plurality of reflective structures capable of reflecting infrared wavelengths, said structures being elongated along an axis of the tubular passage and arranged around the axis. The reflective structures comprise means of filtering by absorption of bands of different wavelengths located in the infrared spectral band.

16 Claims, 3 Drawing Sheets

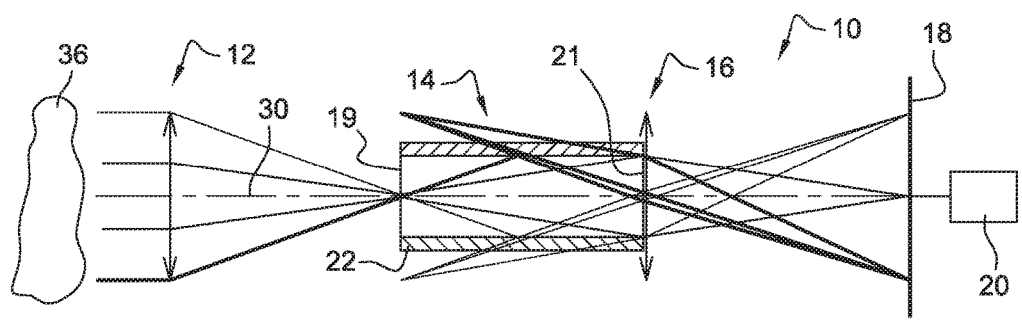
Fig. 1
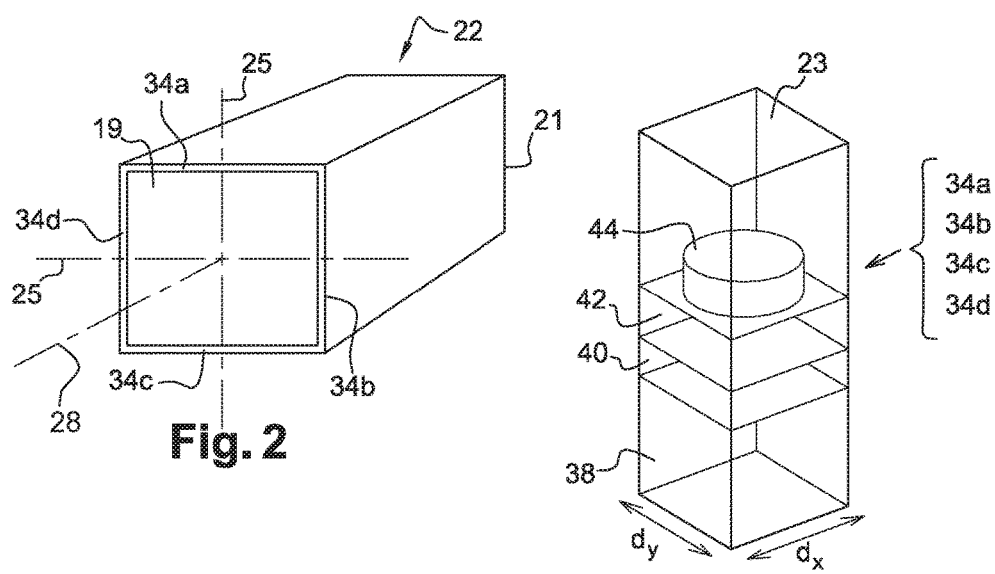
Fig. 2
Fig. 3
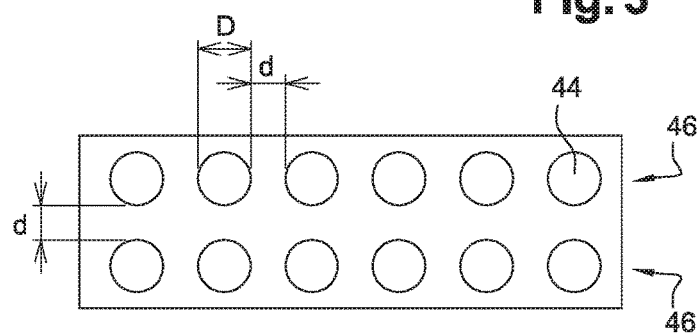
Fig. 4

OPTICAL FILTERING DEVICE FOR DETECTING GAS

FIELD OF THE INVENTION

The invention relates to a device for optical wavelength filtering as well as to a device for remote optical gas detection by means of aforesaid optical filtering device, particularly applicable to monitoring of industrial sites such as chemical plants, refineries, gas storage facilities, etc. The invention is obviously not limited to the aforementioned applications and may, for example, be used in military operations in conflict zones, where harmful gases are likely to be used.

BACKGROUND OF THE INVENTION

Documents ER-A-0544962 and WO 03/044499 disclose an infrared imager associated with optical measurement and reference filters that are placed successively on the imager's optical axis and which have bandwidths containing an absorption line of a desired gas (for measurement filters) or which are complementary to this absorption line (for reference filters). The bottom of the observed area is used as an infrared source and the presence of a desired gas is demonstrated by applying differential processing to infrared images taken through the filters, whereby the processing allows for the concentration of the detected gas to be calculated.

Conveniently, a set of measurement and reference filters is carried by a motorized rotating disc to successively bring the filters onto the imager's optical axis. The images of the area observed in the various spectral hands corresponding to the bandwidths of the filters are acquired sequentially and are separated from one another in time by intervals corresponding to the filter changes. These intervals degrade the overall sensitivity of the imager, which is "blind" during filter changes. Moreover, two successive images of the area observed in the same spectral band are separated by a relatively long period of time, corresponding to the time it takes for the filter wheel to complete a full revolution, which affects the temporal coherence of the images processed and poses problems in the event that rapid movements are detected in the observed area.

Furthermore, the means for motorizing the filter wheel are a source of noise and vibration and degrade the imager's overall reliability. In addition, the use of a movable member, namely the wheel, implies that the level of vibrations transmitted to the device must be controlled in order to prevent the vibrations from affecting the operation of the rotating member.

Also known is a filtering device comprising a tube housing a plurality of elongated mirrors along the axis of the tube and arranged side by side about this axis. The luminous flux coming from an observed area of space propagates in the tube and is reflected on the mirrors, which leads to the formation of a plurality of subimages whose number and shape is a function of the number and the arrangement of the mirrors according to the well-known operating principle of a kaleidoscope. An array of photodetectors is arranged at the outlet of the tube in order to collect the various images. It has thus been proposed to arrange a planar filter comprising a plurality of juxtaposed areas intended to each absorb a different frequency band.

While this configuration allows for temporal filtering to be performed in a plurality of different frequency bands, it turns out that the use of a planar filter is difficult since it requires focusing means to be added downstream of the filter to focus the filtered light rays on an array of detectors.

The present invention particularly aims to avoid these disadvantages in a simple, effective and economical manner.

SUMMARY OF THE INVENTION

The invention relates to an optical filtering device, in particular for remote gas detection, including a member comprising a tubular passage accommodating a plurality of reflective structures capable of reflecting infrared wavelengths, said structures being elongated along the axis of the tubular passage and arranged around this axis, characterized in that the said reflective structures include means of filtering by absorption of bands of different wavelengths located in the infrared spectral band.

The invention thus proposes that the filtering be performed by filtering structures carried by the reflective structures so that the use of a planar filter comprising a plurality of filtering areas is rendered unnecessary. In addition, such an arrangement allows for the space required by the optical filtering device to be reduced in the direction of its optical axis since the filtering means are integrated into the reflective structures.

In comparison with the devices comprising a moving filter wheel, the device's vibrations as well as its sensitivity to the vibrations are also eliminated. The filtering device according to the invention can thus be used in an environment exposed to significant vibrations, such as, for example, a drone or a helicopter, due to the absence of moving parts.

According to the invention, the reflective structures are capable of reflecting at least the infrared wavelengths, i.e. wavelengths between 0.78 µm and 5 mm. In fact, when the optical filtering device is used in a gas detection device, the wavelengths that indicate the presence of a gas to be detected are located in the infrared range. More specifically, the wavelengths of the absorption bands will be located in the mid-infrared range, i.e. between 3 and 50 µm, the near-infrared range being between 0.78 µm and 3 µm and the far-infrared range corresponding to the wavelengths between 50 µm and 5 mm.

According to another characteristic of the invention, at least one of the reflective structures comprises a support carrying the filtering means. In a practical embodiment, the filtering means are formed by a surface plasmon structure.

While the use of a surface plasmon structure is well-known in the case of a band-stop filter operating in transmission, this type of filtering structure has never been used in reflection, and even less in a configuration at grazing angles of incidence, i.e. between about 60° and 80° (measured in relation to the normal line). Moreover, integrating a plasmon structure in a kaleidoscope-type optical filtering device has never been proposed. Lastly, surface plasmon structures are particularly effective in terms of rejection/absorption of a given frequency band.

In one embodiment of the invention, at least one of the plasmon structures comprises a layer of a metallic material in contact with the support and covered with a layer of a dielectric material carrying a plurality of pads dimensioned and spaced relative to each other so as to allow absorption of a given reflected band of wavelengths.

For each plasmon structure, the, pads are distributed over a two-dimensional array with constant spacing between the pads. The pads may have a cylindrical shape with an axis of revolution that is substantially perpendicular to the metallic and dielectric layers. The pads thus have a disc-shaped cross-section. Other shapes are also possible, such as, for example, pads with a square cross-section.

According to another characteristic of the invention, the device comprises at least three reflective structures having absorption bands that differ two by two.

The invention also relates to a device for remote optical gas detection comprising an optical filtering device as described above, a set of photodetectors and optical focusing means on this set of photodetectors of images from an area of space to be observed through the filtering device.

Preferably, the device includes a diaphragm inserted between an inlet lens of the device and the inlet of the tubular passage or between the outlet of the tubular passage and the set of sensing elements.

Depending on the diameter of the diaphragm's aperture, black intermediate areas are thus formed between the images on the array of photodetectors, which facilitates image processing operations by eliminating any coupling between neighbouring sensing elements.

Other details, characteristics and advantages of the invention will appear upon reading the following description given by way of a non-restrictive example while referring to the appended drawings.

BRIEF DESCRIPTION OF THE DRAWINGS

FIG. 1 is a schematic representation of the optical filtering device according to the invention;

FIG. 2 is a schematic perspective view of a tubular passage according to a first embodiment of the filtering device according to the invention;

FIG. 3 is a schematic perspective view of a pad carried by a bilayer material used for surface plasmon filtering;

FIG. 4 is a schematic top view of the pads;

DETAILED DESCRIPTION OF THE INVENTION

Figure 5:
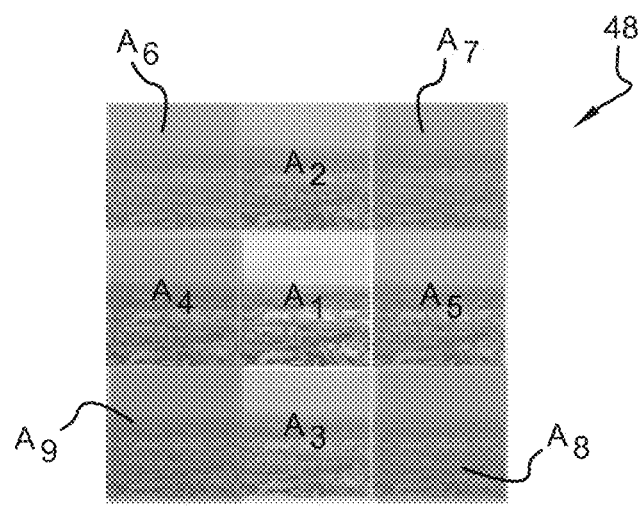
FIG. 5 is a schematic view of the subimages obtained on the photodetector array with a tubular passage according to FIG. 2.

Let us first refer to FIG. 1, which schematically represents a device 10 for remote optical gas detection according to the invention comprising first optical input means 12, such as for example an objective formed by one or several lenses intended to receive an electromagnetic flux coming from an observed area of space and to orient it at the input of a filtering device 14 according to the invention, second optical output means 16 for focusing the electromagnetic flux output by the filtering device onto a set of sensing elements 18, such as photodetectors, connected to calculation and processing means 20.

Figure 6:
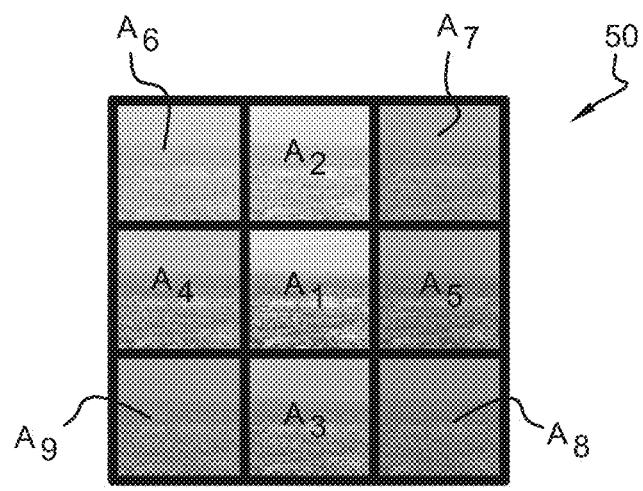
FIG. 6 is a view similar to FIG. 3, a diaphragm being arranged at the inlet of the tubular passage.
Figures 7, 8:
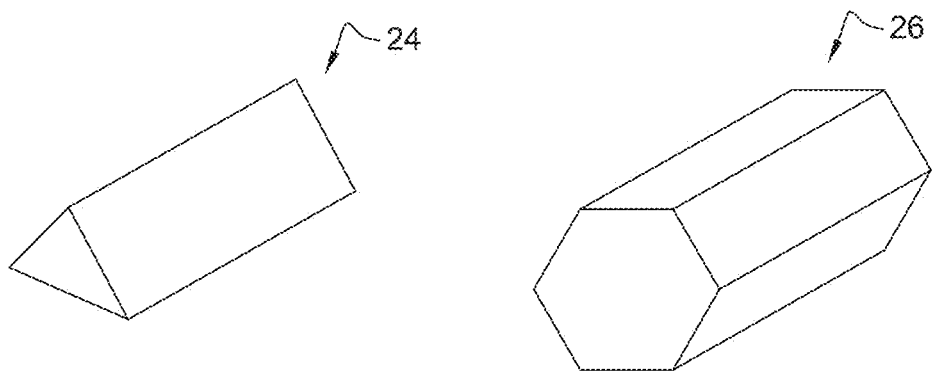
FIGS. 7 and 8 are views of two other possible shapes for a tubular passage housing mirrors.

The optical filtering device 14 comprises a tube 22 that can be, as shown in FIG. 2, of square section defining a tubular passage. The invention is of course not limited to this embodiment and relates, for example, to tubes having a rectangular, triangular 24 (FIG. 6) or hexagonal section 26 (FIG. 7).

The term "tube" is used hereinafter to mean any part defining a tubular passage and capable of accommodating a plurality of reflective structures as will be described below.

The tube 22 thus extends along an axis 28 that coincides with the optical axis 30 of the gas detection device and internally comprises a plurality of planar reflective structures 34a, 34b, 34c, 34d. The reflective structures are elongated in the direction of the optical axis 30. Each inner face of the tube 22 is provided by a reflective structure 34a, 34b, 34c, 34d extending from a first end for forming an inlet of a radiative flux from an observed area of space 36 to a second opposite end forming an outlet of said flux in the direction of the array of sensing elements 18.

According to the invention, each reflective structure 34a, 34b, 34c, 34d comprises a substrate 38 intended to provide a mechanical support function. The reflective structures 34a, 34b, 34c, 34d are planar and extend along the axis 28 of the tubular passage, which comprises an inlet 19 and an outlet 21. Each reflective structure 34a, 34b, 34c, 34d comprises a face 23 intended to be oriented towards the inside of the tubular passage 22. The reflective structures 34a, 34b, 34c, 34d are distributed around the axis 28 of the tubular passage 22 so as to be arranged circumferentially, i.e. around the axis 28 of the tubular passage, one after the other. The reflective structures are thus oriented so that the normal line 25 at each face 23 of a reflective structure 34a, 34b, 34c, 34d is perpendicular to the axis 28 of the tubular passage 22.

Each substrate or support 38 carries filtering means, such as a bilayer structure comprising a metallic layer 40 of a metallic material in contact with the support 38 through a first face and whose second face, opposite the first face, is covered with a dielectric layer 42 of a dielectric material carrying a plurality of pads 44 at the opposite end of the second face of the metallic layer 40 (FIGS. 3 and 4). Each reflective structure 34a, 34b, 34c, 34d is thus comprised of filtering means including the metallic layer 40 of metallic material, the dielectric layer 42 of dielectric material, and the arrangement of pads 44. The metallic layer 40, dielectric layer 42, and pads 44 form a surface plasmon structure (also referred to as a plasmonic mirror).

Thus, an embodiment of the present invention includes a plurality of reflective structures 34a, 34b, 34c, 34d, each reflective structure comprising a support substrate 38 and filtering means that comprises a surface plasmon structure. The surface plasmon structure includes, for example, metallic layer 40, dielectric layer 42, and pads 44 whose dimensions and distribution determine the wavelength band absorbed. More specifically, the pads 44 are arranged in a regular manner on the surface of the dielectric layer 42. Each reflective structure 34a, 34b, 34c, 34d thus comprises several rows 46 of pads 44 that can be aligned in the direction of the optical axis 30.

As shown in FIGS. 3 and 4, the pads 44 are cylinders having an axis of revolution substantially perpendicular to the layers of metallic 40 and dielectric 42 materials.

The absorption band of each plasmon structure can be varied simply by varying the spacing d between two pads 44 and the diameter D of each pad 44 (FIG. 4).

FIG. 5 shows an image 48 of an area of space 36 recorded by the detector array 18 after passing through the square section tube 22 as shown in FIG. 2. FIG. 6 also shows an image 50 and a series of similar images, which are however separated from another by black bands that are obtained by the addition of a diaphragm (not shown) between the first optical means 12 and the inlet of the tube 22.

As can be seen in FIGS. 5 and 6, each image comprises nine subimages A1-A9, whereby the central image A1 corresponds to an unfiltered image of the area of space 36, subimage A2 in the upper position is obtained after reflecting the radiative flux of the area observed 36 onto the lower plasmon structure associated with reflective structure 34e, subimage A3 in the lower position is obtained after reflecting the radiative flux of the area observed 36 onto the upper plasmon structure associated with reflective structure 34a, subimage A4 on the left is obtained after reflecting the radiative flux of the area observed 36 onto the right plasmon structure associated with reflective structure 34b when viewing the tube 22 from its inlet, subimage A5 on the right is obtained after reflecting the radiative flux of the area observed 36 onto the left plasmon structure associated with reflective structure 34d when viewing the tube 22 from its inlet. Subimages A6-A9 located in the corners correspond to reflections of the radiative flux on two adjacent mirrors and thus to two absorptions in two different infrared wavelength bands.

The gas detection device according to the invention thus comprises a plurality of reflective structures 34a, 34b, 34c, 34d, capable of reflecting infrared wavelengths and of absorbing a given band of infrared wavelengths, which includes the absorption line of a gas to be detected. Thus, using a device according to the invention, several types of gas can be detected simultaneously. In addition, simultaneously obtaining the unfiltered image of the observed area of space corresponding to the central subimage A1 on the detector array, as well as the filtered lower subimage A3, upper subimage A1, right subimage A5, and left subimage A4, allows for deducing by subtraction the presence or absence of a gas to be detected that has an infrared absorption band located in one of the absorbing bands of the plasmon structures.

Figure 9:
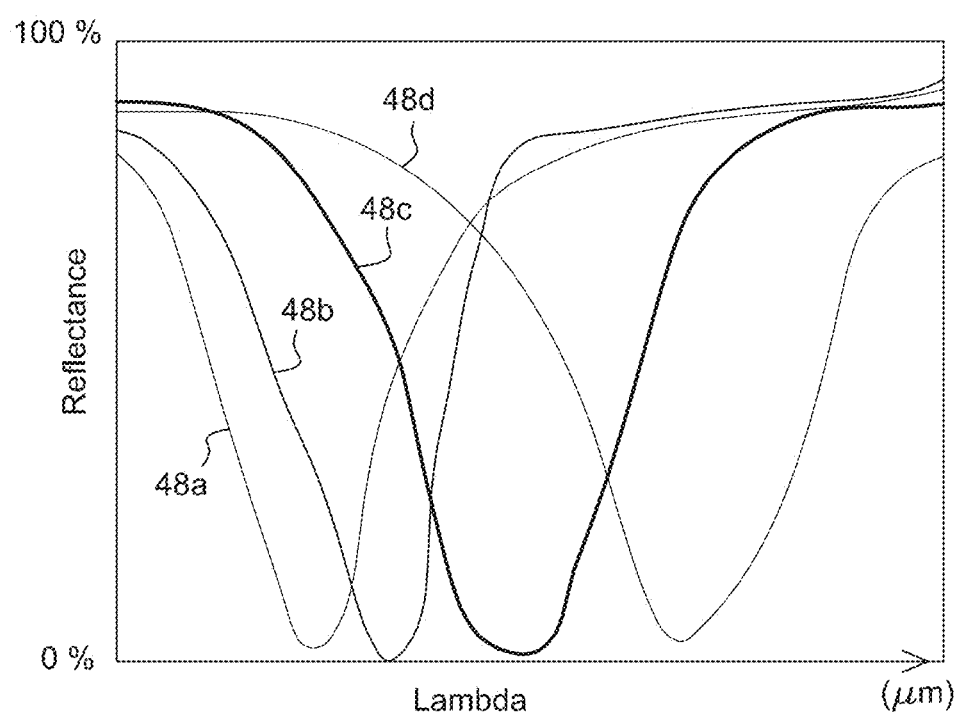
FIG. 9 represents a graph comprising four curves, each representing the evolution of the reflection factor as a function of the wavelength for a given reflective structure.

FIG. 9 represents a graph whose abscissa represents the wavelength in micrometers, in the infrared radiation band, and the ordinate represents the reflectance. Each curve 48a, 48b, 48c, 48d represents the change in reflectance for one of the mirrors as shown in FIG. 2.

In a practical embodiment, the support is thus made of silicon, the metal layer is made of chromium, the dielectric layer is made of silicon and the pads can be made of chromium.

The device according to the invention allows for a large angle of aperture for real-time gas detection. In order to improve the analysis of the gas to be detected as well as of its concentration, the device according to the invention 10 could be combined with a Fourier transform spectroscope that has a small angle of aperture, but which allows for the compounds and their respective concentrations to be accurately detected in a given direction of the area of space analysed. An array of micromirrors could be used for this purpose to first orient the radiative flux originating from the observed area of space towards the plasmonic filter gas detection device and, in the event that a gas is positively detected, to orient some of the micromirrors in a second position to allow for a portion of the flux to be oriented towards the Fourier transform spectroscope.

Note that the cross-section of the tubular passage described previously is constant over its entire length. However, it would be conceivable to have a tube with a downstream tapering (or swelling) cross-section, i.e. in the direction in which light is propagated through the device, in the direction of the sensing elements. The effect obtained would thus be similar to that described with reference to the image in FIG. 6 when a diaphragm is added.

Having described the invention, the following is claimed:

1. An optical filtering device for remote gas detection, the device comprising:
    a member comprised of a plurality of reflective structures that define a tubular passage, said plurality of reflective structures being planar and elongated along an axis of the tubular passage and arranged around said axis,
    wherein said plurality of reflective structures are capable of reflecting infrared wavelengths, each of said reflective structures including respective filtering means for filtering radiative flux by absorption of bands of different wavelengths located in the infrared spectral band.

2. The device of claim 1, wherein at least one of the reflective structures includes a support substrate for supporting the filtering means.

3. The device of claim 2, wherein at least one of the reflective structures has filtering means comprised of a surface plasmon structure that includes:
    a metallic layer comprised of a metallic material in contact with the support substrate,
    a dielectric layer comprised of a dielectric material, and
    a plurality of pads arranged on a surface of the dielectric layer, said plurality of pads dimensioned and spaced relative to each other so as to allow absorption of a given reflected band of wavelengths.

4. The device of claim 3, wherein the plurality of pads are distributed over a two-dimensional array with constant spacing between the pads.

5. The device of claim 3, wherein the plurality of pads have a cylindrical shape with an axis of revolution that is substantially perpendicular to the metallic layer and the dielectric layer.

6. The device of claim 1, wherein the device includes at least three of said reflective structures, the respective filtering means of each of said reflective structures has an absorption band that is different from an absorption band of the respective filtering means of the other said reflective structures.

7. The device of claim 1, wherein the tubular passage has a square cross-section, a rectangular cross-section, a triangular cross-section or a hexagonal cross-section.

8. A device for remote optical gas detection comprising:
    an optical filtering device for remote gas detection, comprising:
        a member comprised of a plurality of reflective structures that define a tubular passage, said plurality of reflective structures being planar and elongated along an axis of the tubular passage and arranged around said axis,
        wherein said plurality of reflective structures are capable of reflecting infrared wavelengths, each of said reflective structures including respective filtering means for filtering radiative flux by absorption of bands of different wavelengths located in the infrared spectral band;
    a plurality of sensing elements; and
    optical means for focusing on the plurality of sensing elements images from an area of space to be observed through the optical filtering device.

9. The device for remote optical gas detection of claim 8, wherein the device for remote optical gas detection further comprises a diaphragm inserted between an inlet lens and an inlet of the tubular passage.

10. The device for remote optical gas detection of claim 8, wherein the device for remote optical gas detection further comprises a diaphragm inserted between an outlet of the tubular passage and the plurality of sensing elements.

11. The device for remote optical gas detection of claim 8, wherein the tubular passage has a square cross-section, a rectangular cross-section, a triangular cross-section or a hexagonal cross-section.

12. The device for remote optical gas detection of claim 8, wherein at least one of the reflective structures includes a support substrate for supporting the filtering means.

13. The device for remote optical gas detection of claim 8, wherein at least one of the reflective structures includes filtering means comprised of a surface plasmon structure that includes:
  a metallic layer comprised of a metallic material,
  a dielectric layer comprised of a dielectric material, and
  a plurality of pads arranged on a surface of the dielectric layer, said plurality of pads dimensioned and spaced relative to each other so as to allow absorption of a given reflected band of wavelengths.

14. The device for remote optical gas detection of claim 13, wherein the plurality of pads are arranged in a plurality of rows, said pads aligned in a direction of an optical axis of the device for remote optical gas detection.

15. The device for remote optical gas detection of claim 8, wherein the plurality of sensing elements are arranged in an array, said optical means respectively focusing subimages of said image on each of the sensing elements.

16. The device for remote optical gas detection of claim 15, wherein the subimage focused on the sensing element located at a center of said array corresponds to an unfiltered image from the area of the space to be observed.

* * * * *